United States Patent [19]
Blythe

[11] Patent Number: 5,908,402
[45] Date of Patent: Jun. 1, 1999

[54] METHOD AND APPARATUS FOR DETECTING TUBE OCCLUSION IN ARGON ELECTROSURGERY SYSTEM

[75] Inventor: Robert Lewis Blythe, Longmont, Colo.

[73] Assignee: Valleylab, Boulder, Colo.

[21] Appl. No.: 08/792,054

[22] Filed: Feb. 3, 1997

[51] Int. Cl.$^6$ .................................................. A61M 37/00
[52] U.S. Cl. .............................. 604/26; 606/41; 600/560
[58] Field of Search ................................. 606/1, 41, 42, 606/45, 46, 48–50; 604/23, 26, 27, 28; 600/560

[56] References Cited

U.S. PATENT DOCUMENTS

| | | |
|---|---|---|
| 3,595,239 | 7/1971 | Petersen . |
| 3,688,770 | 9/1972 | O'Neill . |
| 3,699,967 | 10/1972 | Anderson . |
| 3,885,590 | 5/1975 | Ford et al. . |
| 4,040,426 | 8/1977 | Morrison, Jr. . |
| 4,057,064 | 11/1977 | Morrison, Jr. et al. . |
| 4,060,088 | 11/1977 | Morrison, Jr. et al. . |
| 4,781,175 | 11/1988 | McGreevy et al. . |
| 4,874,362 | 10/1989 | Wiest et al. . |
| 4,971,034 | 11/1990 | Doi et al. . |
| 5,047,010 | 9/1991 | Ams et al. . |
| 5,088,997 | 2/1992 | Delahuerga et al. . |
| 5,098,375 | 3/1992 | Baler . |
| 5,139,478 | 8/1992 | Koninckx et al. . |
| 5,217,457 | 6/1993 | Delahuerga et al. . |
| 5,244,462 | 9/1993 | Delahuerga et al. . |
| 5,246,419 | 9/1993 | Absten . |
| 5,292,304 | 3/1994 | Mantell et al. . |
| 5,427,104 | 6/1995 | Briend et al. . |

Primary Examiner—Michael Peffley

[57] ABSTRACT

A method and apparatus detect occlusion in a tube to a passage into a body cavity. An argon gas supply output received by plural selectable flow orifices so one or more of the orifices delivers predetermined metered gas. A duct with a volume of gas selectively provides metered gas to the passage. The tube connects the passage and the duct periodically so a duct pressure transducer can signal. A circuit tests signals of tube equalization with a back pressure. A three way valve controlled by the circuit connects the duct transducer to gas metered to the cavity. The valve alternatively connects the duct transducer to the tube to equalize the tube with metered gas to the back pressure. A monitor of the signals determines the rate of pressure change after the valve connection. The monitor indicates pressure equalization after a timed interval with a timer to establish intervals for checking back pressure. The monitor remembers cavity pressure before connecting the duct transducer to the metered gas and compares remembered pressure with the back pressure after each test interval. Plural orifices provide specific gas flows to the handset and the valve for equalizing them with metered gas as a function of the flow. Connecting plural orifices to meter gas output, delivering the metered gas output with one or more of the orifices, containing the volume of gas in the duct connected to the metered gas output, selectively connecting the duct to the passage, connecting the tube to the passage with the duct and the transducer to periodically signal are steps. Coupling the circuit to one or more orifices, equalizing the tube with back pressure in response to the signals and coupling the transducer to the metered gas output are steps. Connecting the duct transducer to the tube permits periodic back pressure equalization with metered gas output, signaling the monitor with the transducer, determining periodically the rate of pressure change in the tube by the transducer, indicating in the interval with the monitor equalized tube pressure and remembering cavity pressure before connecting the metered gas output and the transducer for intervals and providing specific flows to the handset and the valve to make the back pressure a function of the selectable flow are steps.

18 Claims, 3 Drawing Sheets

PERITONEAL TUBE NOT OCCLUDED

METHOD AND APPARATUS FOR DETECTING TUBE OCCLUSION IN ARGON ELECTROSURGERY SYSTEM

FIELD OF THE INVENTION

This relates to an apparatus and method for measuring a peritoneal connection with pressure applied to a percutaneous passageway into the patient's abdominal cavity, more particularly to determine in the patency of the passageway.

BACKGROUND OF THE DISCLOSURE

The invention relates to improvements in the operation of electrosurgical instruments for coagulating and cutting biological tissue with argon. In particular, the invention relates to a device for enhancing the safety and efficiency of a hand-operated electrosurgical handset which is used in conjunction with a flow of argon to perform the desired coagulation by electrosurgical fulguration or to provide electrosurgical cutting and to an improved method for performing electrosurgical operations in the abdominal cavity.

Electrosurgical fulguration comprises the application of electric sparking to biological tissue, for example, human flesh or the tissue of internal organs, without significant cutting. The sparking is produced by bursts of radio-frequency electrical energy generated from an appropriate electrosurgical generator. Generally, fulguration is used to dehydrate, shrink necrose or char the tissue, which operations are primarily to stop bleeding and oozing, or otherwise to seal the tissue. These operations are generically embraced by the term "Coagulation". Electrosurgical cutting comprises electric sparking to tissue with a cutting effect.

As used herein the term "electrosurgical handset or handset" is intended to mean an instrument comprising a surgical handpiece to which is attached an electrode (the "active electrode"), that may be detachable or fixed. The handset may be operated by a handswitch or a foot switch. The active electrode is an electrically conducting element usually elongated in the form of a thin flat blade with a pointed or rounded distal end, or an elongated narrow cylindrical needle that may be solid or hollow with a flat, rounded, pointed or slanted distal end. The term "electrode" when used herein will generally refer to the active electrode. Electrodes as blade electrodes, loop or snare electrodes, needle electrodes and ball electrodes are available.

The handset is connected to a suitable electrosurgical generator which generates the high frequency electrical energy necessary for the operation of the electrosurgical handset. An electrosurgical generator suitable for use with electrosurgical electrodes and handsets is disclosed in U.S. Pat. No. 3,699,967, the disclosure of which is incorporated herein by reference. When an operation is performed on a patient with a handset, electrical energy from the electrosurgical generator is conducted through the active electrode to the tissue at the site of the operation and then through the patient to a return electrode, placed at a convenient place on the patient's body, to return via a patient pad or plate made of conductive material to the electrosurgical generator. A suitable circuit is illustrated schematically in U.S. Pat. No. 3,699,967.

The use of a stream of argon gas in conjunction with an electrosurgical electrode is in U.S. Pat. No. 4,060,088 wherein an electrosurgical method and apparatus for coagulating tissue by fulguration that involves establishing an electrical discharge in argon gas flowing through a tubular electrode to which high-frequency electrical energy is applied.

U.S. Pat. No. 4,040,426 discloses a method and apparatus wherein the argon gas flow disposed adjacent the end of an active electrode produce a primary electrical discharge in the gas and the apparatus includes a second electrode, electrically isolated from any source of biasing potential, which facilitates the establishment of an auxiliary electrical discharge from an electrostatic charge generated by the argon gas. U.S. Pat. No. 4,057,064 discloses a method and apparatus for producing coagulation of tissue with a flow of argon gas and an active electrode.

Gas surgical pencils have a pair of switches that start and stop argon flow as disclosed in U.S. Pat. No. 5,217,457; U.S. Pat. No. 5,244,462 and U.S. Pat. No. 5,088,997 all assigned to the same assignee, Valleylab Inc Boulder, Colorado as this disclosure. The switch for directing argon flow mounts on the electrosurgical pencil. A gas line for argon and a pair of switches for the electrosurgical generator coagulation or cut wave forms are on the pencil. The argon electrosurgical pencil includes an electrical cable with wires for connection directly to the gas surgical unit to trigger the flow of argon gas when the electrosurgical energy is called for by the surgeon. The gas delivery control is on the pencil and controls the gas delivery from the separate on and off switch buttons and wires connecting to circuits integral with the gas surgical unit. In addition to the three wires connected between the argon electrosurgical pencil and the gas surgical unit, there is another wire for providing electrosurgical energy from the electrosurgical generator. Cut and coagulation wave forms are controlled by buttons therefor on the gas surgical pencil.

U.S. Pat. No. 4,781,175 discloses an electrosurgical technique for achieving coagulation involving conducting a predetermined ionizable gas not containing oxygen in a jet to tissue and conducting electrical radio-frequency energy in ionized conductible pathways in the gas jet.

Argon supplies those metering orifices and valves provide varying flow rates of argon gas to the electrosurgical tip. The concept of using metering orifices and valves is shown in U.S. Pat. No. 5,427,104 wherein the volume of flow is metered. A three way valve connects to receive the metered volume. U.S. Pat. No. 3,688,770 discloses valves and restrictions. U.S. Pat. No. 3,885,590 has a pressure regulator and a metering orifice with a valve to bleed to atmosphere excess pressure and protect the patient. U.S. Pat. No. 5,292,304 discloses digital control of the valves before the metering orifices in an insufflator for providing various flows. There are a variety of well known approaches for controlling gas flow by metering orifices.

Percutaneous surgery through a trocar inserted cannula and particularly with an opening through the external tissue of a patient, such as an abdominal wall has become an important means to minimize the extent of surgical invasion. The lessening of invasion improves the cosmetic result, shortens recovery and lowers the cost. Endoscopic or laparoscopic internal surgical procedures and equipment are available and in use for a variety of medical operations including gall bladder, bowel and gynecological surgery.

U.S. Pat. No. 3,595,239 discloses a catheter tube having an obturator in the form of an electrode passing coaxially therethrough. The obturator electrode is connected to an electrosurgical generator in order to provide high frequency energy used to divide or cut tissue thereby forming a passage for the catheter coaxially about the obturator to pass therewith through the tissue. The tip of the obturator extends beyond the catheter tip and cuts the path for its passage. The catheter moves along with the obturator electrode by means of a ring disposed about the obturator proximal to the tip and inside the tip of the catheter.

U.S. Pat. No. 4,874,362 has a system and its use for controlling the addition of insuflation gas. The detected gas flow at a regulated pressure is repeatedly compared at successive clock intervals with a preset flow rate value and regulated to a level of 50 millimeters of mercury higher than the preset nominal pressure. The purpose of this patent is to eliminate magnetic valves and to allow for the constant control, monitoring and delivery of flow as required to the body cavity. The system looks at the pressure and adjusts the input or flow of gas on a frequent basis as controlled by pulsations established by the software in this computer operated circuit.

U.S. Pat. No. 4,971,034 checks pressure on a suction tube communicating with a channel through an endoscope against a reference pressure so that a control may operate the suction source to regulate the pressure between that found and that desired. U.S. Pat. No. 5,047,010 discloses an insuflation control including a fluid supply with a pressure valve for insuflation of the body cavity and means for measuring the actual value of fluid pressure in the cavity. A circulation pump connected to a filter in communication with the body cavity for drawing off fluid and delivering it back to the probe through a second fluid circuit wherein the two circuits have common portion extending to the probe and a means associated with the pump compensates for dynamic pressure independently of the delivered flow by response to partial vacuum on the inlet side of the pump.

U.S. Pat. No. 5,098,375 has a pressure sensor control and valve operated thereby to regulate the addition of gas to make up for that which is absorbed and that which is lost through leakage and debris removal, i.e., constant insuflation pressure. U.S. Pat. No. 5,139,478 has a source of insuflation gas and a suction unit, a delivery line between source and a gas inlet of a surgical laser equipped endoscope, part of endoscopic tube is introducable into the body cavity with the insuflation gas from the source. Pressure adjustment means on the delivery line limit the pressure gas insuflated for maximum flow and an exhaust for the gas in the body cavity connects to the suction unit and passes through the endoscope. If the flow is greater than two liters per minute per centimeter of water column, insuflation gas pressure is recirculated.

U.S. Pat. No. 5,246,419 has an intra-abdominal insuflation apparatus and a plurality of gas delivery tubes connected in parallel to a source of insuflation gas for the body cavity, a means for measuring the insuflation pressure in the cavity separate from the flow of gas in each of the tubes and plurality of means for controlling flow of insuflation gas to the pressure sensing means and automatically adjusting the flow independently in each of the tubes.

It has been found that if at least one stream or jet of filtered argon gas when directed into the abdominal cavity may change the insuflation pressure. The argon electrosurgical handset may be used both for cutting and coagulation and the delivery of argon can change the insuflation pressure or clog a passage way from the abdominal cavity.

The present invention provides improvements in abdominal cavity surgery with the techniques disclosed in the above patents, but since the basic concept of initiating an electrical discharge is an argon gas flow and the general circuitry for carrying out the procedure is involved with apparatuses and methods of the present invention, the disclosure in each and all of the aforementioned patents is incorporated herein by reference.

SUMMARY OF THE INVENTION

An apparatus within an argon electrosurgery delivery system, preferably detects an occlusion in a monitored pressure tube connected to a percutaneous passageway into the abdominal cavity of a patient. The apparatus has an argon gas supply output with a plurality of selectable flow orifices connected to receive the argon gas supply output. Preferably one or more of the plurality of selectable flow orifices delivers a predetermined metered argon gas output. A duct preferably contains a volume of argon gas. The duct most preferably selectively connects in fluid communication with the predetermined metered argon gas output. The duct may be selectively connectable in fluid communication with the percutaneous passageway into the abdominal cavity.

A tube is preferably connected in fluid communication between the percutaneous passageway into the abdominal cavity and connected to the duct. A pressure transducer may be connected in fluid communication with the duct and the duct periodically connected to the tube. The pressure transducer preferably connects for periodically receiving and responding with pressure signals from tube. A control circuit may be coupled electrically to one or more of the plurality of selectable flow orifices for receipt of the predetermined metered argon gas output. The control circuit is preferably connected for equalizing within the tube with a back pressure in response to the pressure signals from the pressure transducer. The control circuit is in the preferred embodiment electrically coupled to the pressure transducer for receiving the tube pressure signals to test equalization.

An electrically operable a three way normally closed valve may be electrically coupled to the control circuit for connecting the pressure transducer and duct to the predetermined metered argon gas output to the abdominal cavity. The electrically operable three way normally closed valve may be preferably coupled to the control circuit for alternatively connecting the pressure transducer and duct to the tube to selectively permit periodic fluid communication with the tube to equalize the tube with the predetermined metered argon gas output to the back pressure. A monitor is in the preferred embodiment electrically coupled to the pressure transducer to receive signals from the pressure transducer. The monitor may be used for periodically determining the rate of pressure change in the tube after the electrically operable three way normally closed valve connects the tube to the pressure transducer and duct. The monitor for indicating if the pressure in the tube is equalized after a timed interval.

The monitor can include a timer for establishing time intervals for the periodic checking changes in the back pressure in the tube to test equalization. An alarm is preferably coupled to the monitor to indicate lack of pressure equalization between the abdominal cavity and the duct after a test interval. The predetermined metered argon gas output may connect to the electrically operated three way normally closed valve also connects to an argon electrosurgical handset for laparoscopic application within the abdominal cavity. The monitor might include a computer to remember the abdominal cavity pressure before connecting the duct and the pressure transducer to the predetermined metered argon gas output. The computer most preferably compares the remembered abdominal cavity pressure with the back pressure following the test interval.

The tube may have a volume selected to maximize any monitored pressure difference between the duct and the tube. The plurality of selectable flow orifices can include one or more metering orifices to provide specific gas flows to the argon handset and the electrically operable three way normally closed valve. The computer can make the back pressure equalization with the predetermined metered argon gas output a function of the selectable flow rate. An audible alarm is preferably coupled to the monitor.

A method may use an apparatus within an argon electrosurgery delivery system. The method preferably detects an occlusion in a monitored pressure tube connected to a percutaneous passageway into the abdominal cavity of a patient. Supplying argon gas to an output may be a step of the method. The method may have the step of connecting a plurality of selectable flow orifices to receive the argon gas supply output. Another step might be delivering with one or more of the plurality of selectable flow orifices a predetermined metered argon gas output. Containing within a duct a volume of argon gas by selectively connecting the duct in fluid communication with the predetermined metered argon gas output can be a step. The method might include the step of selectively connecting the duct in fluid communication with the percutaneous passageway into the abdominal cavity. The step of connecting a tube in fluid communication between the percutaneous passageway into the abdominal cavity by connecting the tube to the duct can be in the method. The method may have the step of connecting a pressure transducer in fluid communication with the duct and periodically connected to the tube and the pressure transducer for periodically receiving and responding with pressure signals from tube.

It is preferable to include the step of coupling electrically a control circuit to one or more of the plurality of selectable flow orifices. Equalizing, within the tube, a back pressure in response to the pressure signals from the pressure transducer can be a step. The step of connecting the pressure transducer for receiving the tube pressure signals to test equalization may be followed. The method may have the step of coupling electrically an electrically operable three way normally closed valve to the control circuit for connecting the pressure transducer and duct to the predetermined metered argon gas output to the abdominal cavity.

It is preferred to have the step of coupling electrically the electrically operable three way normally closed valve to the control circuit for alternatively connecting the pressure transducer and duct to the tube to selectively permit periodic fluid communication with the tube to equalize the tube with the predetermined metered argon gas output to the back pressure. Coupling electrically a monitor to the pressure transducer to receive signals from the pressure transducer may be a step. It is preferred to have the step of determining periodically with the monitor the rate of pressure change in the tube after the electrically operable three way normally closed valve connects the tube to the pressure transducer and duct. The method may include the step of indicating with the monitor if the pressure in the tube is equalized during a timed interval.

The method can have the step of establishing with a timer in the monitor time intervals for the periodic checking changes in the back pressure in the tube to test equalization. The method may use the step of coupling an alarm to the monitor to indicate lack of pressure equalization between the abdominal cavity and the duct after a test interval. The step of connecting an argon electrosurgical handset for laparoscopic application within the abdominal cavity to the predetermined metered argon gas output to the electrically operated three way normally closed valve may be in the method. The method might include the step of including a computer in the monitor to remember the abdominal cavity pressure before connecting the predetermined metered argon gas output and the pressure transducer to the predetermined metered argon gas output, the computer to compare the remembered abdominal cavity pressure with the back pressure after the test interval.

The method may preferably have the step of maximizing with a selected volume for the tube any monitored pressure difference between the duct and the tube. The method preferably has the step of including one or more metering orifices in the plurality of selectable flow orifices to provide specific gas flows to the argon handset and the electrically operable three way normally closed valve. It is preferred that method include the step of making the predetermined metered argon gas output back pressure a function of the selectable flow with the computer. The method might have the step of coupling an audible alarm to the monitor.

DETAILED DESCRIPTION OF THE INVENTION

Figure 1:
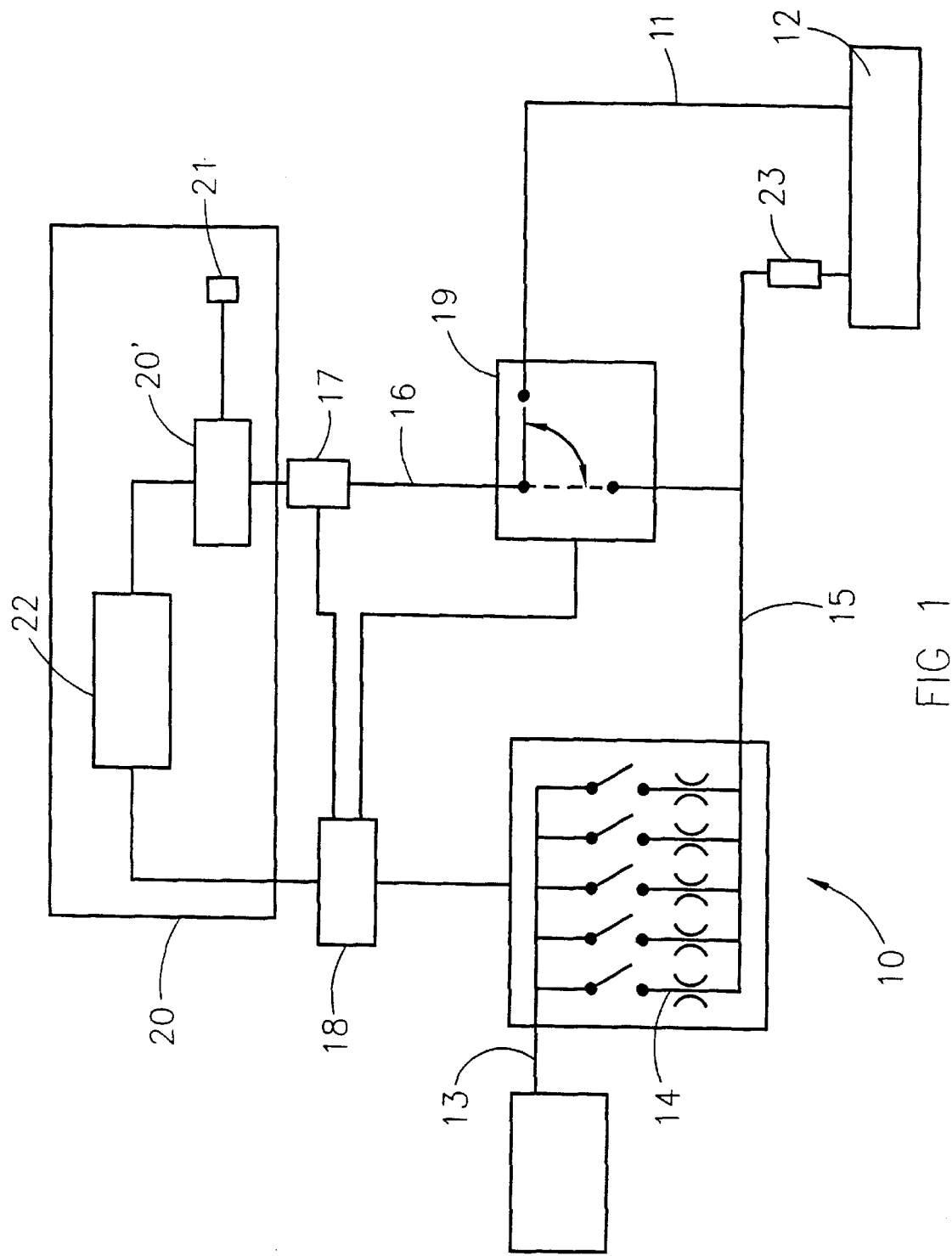
FIG. 1 is a schematic view of the system for occlusion testing argon assisted electrosurgery.

An apparatus 10 in FIG. 1 is shown as a schematic view of the system for occlusion testing argon assisted electrosurgery. The apparatus 10 is used as part of an argon electrosurgery delivery system. The preferred embodiment is in the Force Argon II product of Valleylab Inc, of Boulder, Colo. The apparatus 10 detects occlusions within a monitored pressure tube 11 connected to a percutaneous passageway into the abdominal cavity 12 of a patient. The apparatus 10 has an argon gas supply output 13 and a plurality of selectable flow orifices 14 connected to receive the argon gas supply output 13. The preferred flow orifices 14 are from Digital Valve, Engineering Measurement Co., Longmont Colo. as their part number 200-B05-01-05-1. One or more of the plurality of selectable flow orifices 14 are used as desired for delivery of a predetermined metered argon gas output 15.

A duct 16, shown in FIG. 1, contains a volume of argon gas. The duct 16 selectively connects in fluid communication with the predetermined metered argon gas output 15. Similarly, the duct 16 is selectively connectable in fluid communication with the percutaneous passageway into the abdominal cavity 12, as in FIG. 1. A tube 11 connects in fluid communication between the percutaneous passageway into the abdominal cavity 12 and the tube 11 is also connectable to the duct 16.

Figure 2:
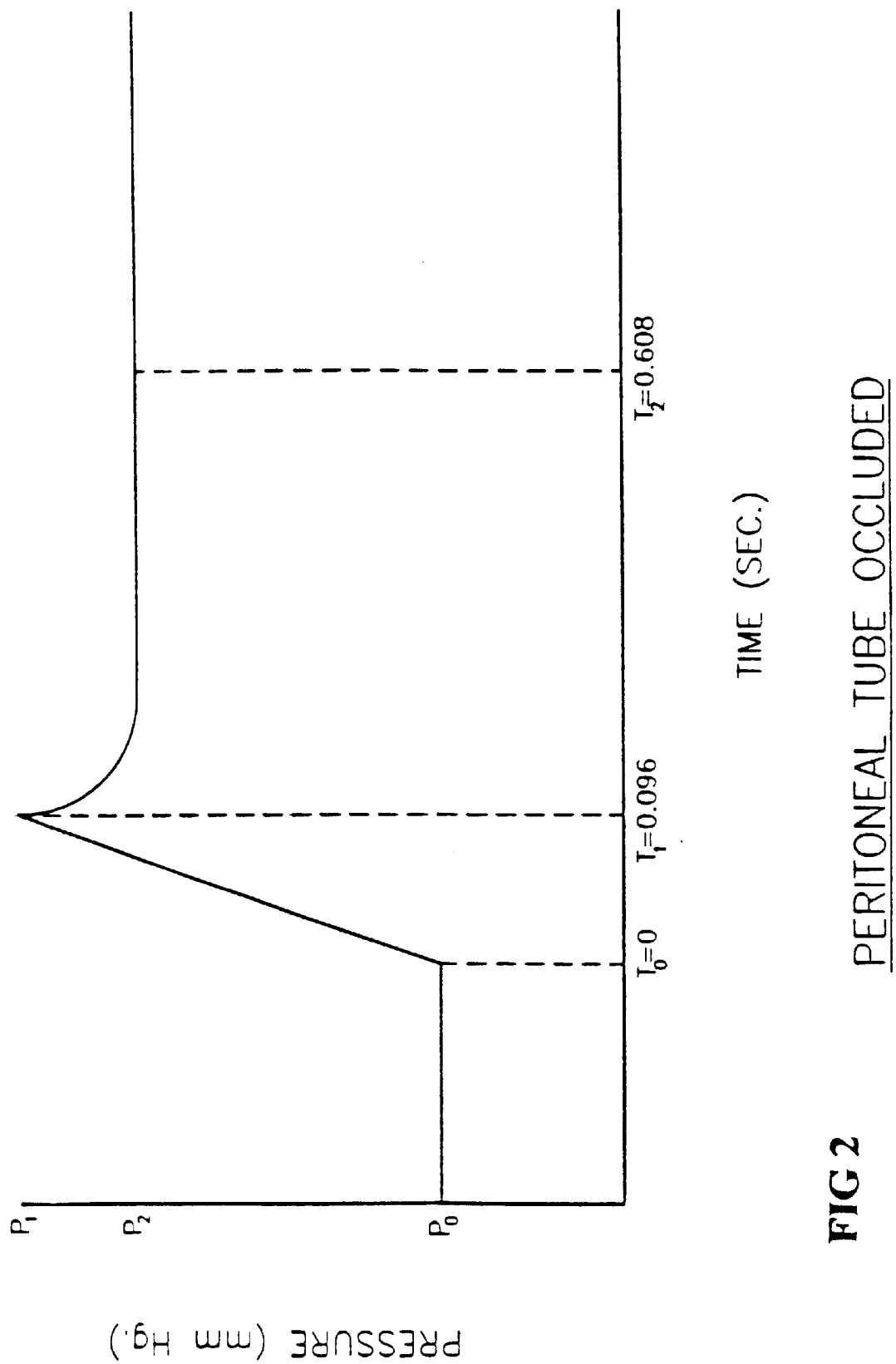
FIG. 2 is a time verses pressure graph with the results of a typical test to find that the tube is occluded.
Figure 3:
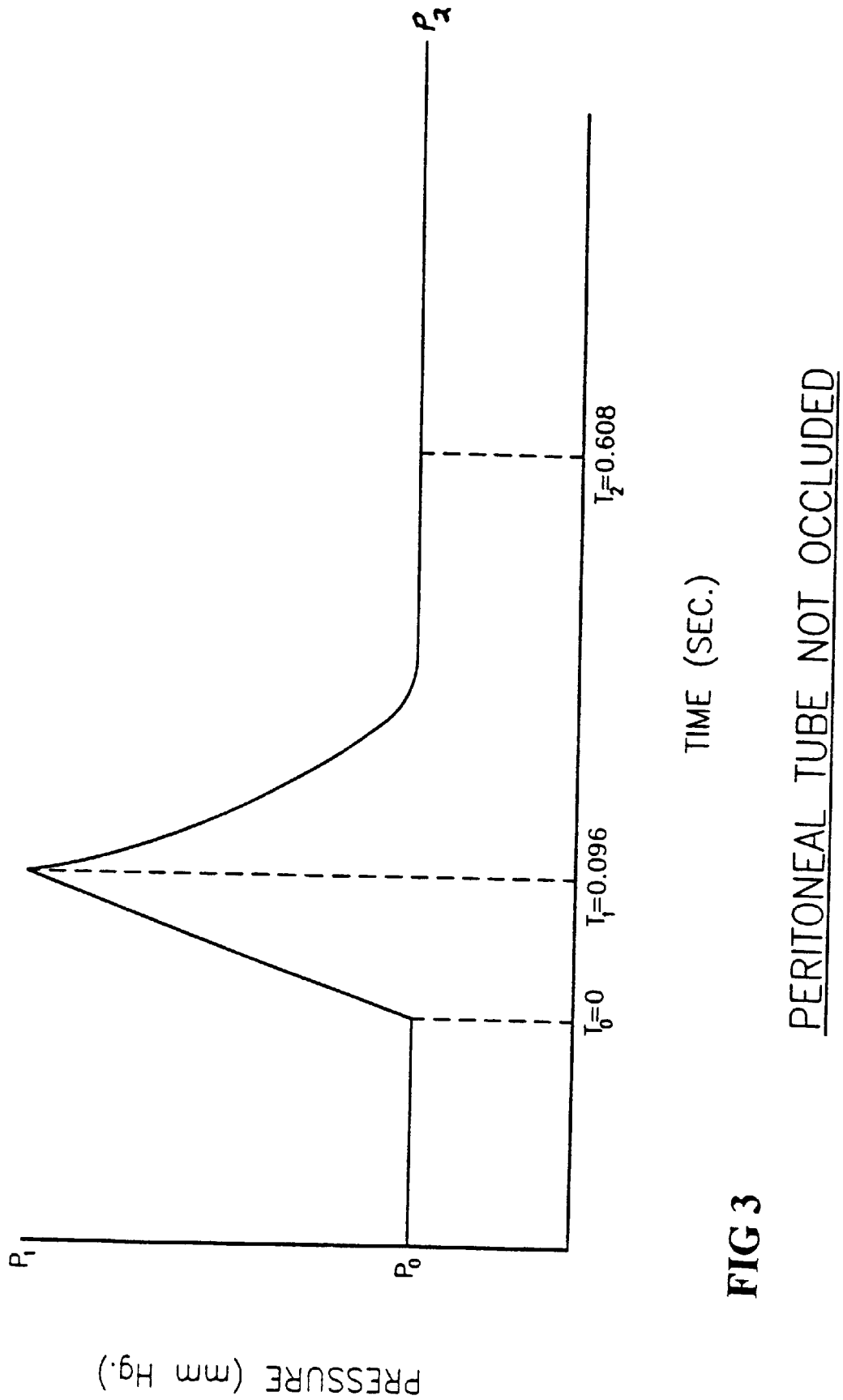
FIG. 3 is a time verses pressure graph with the results of a typical test finding that the tube is not occluded.

A pressure transducer 17, shown schematically in FIG. 1, connects in fluid communication with the duct 16, and the duct 16 periodically connects to the tube 11. The pressure transducer 17 can be an IC Sensors of Milpitas, Calif., part number 1210-A-002-G-3L for periodic connection to receive and respond with pressure signals from tube 11. Pressure signals are shown in FIGS. 2 and 3 that are time verses pressure graphs. A control circuit 18 couples electrically to one or more of the plurality of selectable flow orifices 14 to select the predetermined metered argon gas output 15.

An electrically operable three way normally closed valve 19 electrically couples to the control circuit 18 for connecting the pressure transducer 17 and duct 16 to the predetermined metered argon gas output 15 to the abdominal cavity 12. The preferred three way normally closed valve 19 is from Honeywell Skinner of New Britain, Conn. as part number 3131 BBNINN00. The three way normally closed terminology used herein for the valve 19 is the manufacture's and may be an industry standard. For purposes of this disclosure it means that the three way normally closed valve 19 connects the duct 16 with the predetermined metered argon gas output 15 or the tube 11 as shown in FIG. 1. In shifting from one to the other the three way normally closed valve 19 closes the unconnected path.

For automatic operation, the electrically operable three way normally closed valve 19 couples with the control circuit 18 for alternatively connecting the pressure transducer 17 and the duct 16 with the tube 11 or with the predetermined metered argon gas output 15. A monitor 20 electrically couples to the pressure transducer 17 to receive signals from the pressure transducer 17; this is schematically shown in FIG. 1. The monitor 20 periodically determines the rate of pressure change in the tube 11 after the electrically operable three way normally closed valve 19 connects the tube 11 to the pressure transducer 17 and duct 16. The monitor 20 indicates if the pressure in the tube 11 is equalized after a timed interval. The monitor 20 includes a timer 20' for establishing time intervals for the periodic checking of changes in the back pressure in the tube 11 to test equalization.

An alarm 21 is coupled to the monitor 20 to indicate lack of pressure equalization as shown in FIG. 2 between the abdominal cavity 12 and the duct 16 after the test interval, as shown on the timer 20'. Each test interval is defined by the time interval between $T_0$ and $T_2$, as represented by the graphs in FIGS. 2 and 3. In the preferred embodiment, the test interval repeats every 5 seconds while metered gas is flowing. The predetermined metered argon gas output connects to the electrically operated three way normally closed valve 19 and also connects to an argon electrosurgical handset 23 for laparoscopic application within the abdominal cavity 12; this is shown in FIG. 1.

The monitor 20 includes a computer 22 to remember the abdominal cavity 12 pressure, $P_0$ in FIGS. 2 and 3 before connecting the duct 16 and the pressure transducer 17 to the predetermined metered argon gas output. The computer 22 compares the remembered abdominal cavity 12 pressure $P_0$ with the back pressure $P_2$, which occurs after the equalization of the tube 11 to the back pressure.

In the preferred embodiment, the apparatus 10 checks for occlusion in the tube 11 approximately every 5 seconds while gas is flowing in the metered argon gas output 15. The valve 19 connects the duct 16 with the tube 11 while the pressure in the tube 11 is measured by the pressure transducer 17 and shown as $P_0$ in FIGS. 2 and 3. At time $T_0=0$, the pressure $P_0$ is recorded by the computer 22, and the valve 19 is subsequently switched to connect the duct 16 with the metered argon gas output 15. The pressure from the metered argon gas output 15, also called the back pressure, is normally higher than the pressure in the tube 11. Thus, the duct 16 is charged with the higher back pressure as shown by $P_1$ in FIGS. 2 and 3. The valve remains in a position connecting the duct 16 with the metered output 15 for a period of 96 milliseconds.

At the end of 96 milliseconds, the duct 16 has been fully charged to the back pressure $P_1$, and the valve 19 is switched to connect the duct 16 with the tube 11. When the duct 16 and the tube 11 are connected, the gas reaches an equilibrium pressure in their combined volume. This is shown as a pressure drop from $P_1$ to $P_2$ in FIGS. 2 and 3. After an additional 512 milliseconds, corresponding to T=608 milliseconds in FIGS. 2 and 3, the pressure transducer 17 measures the new equilibrium pressure $P_2$, which is recorded by the computer 22.

The computer 22 compares $P_0$ with $P_2$. If the tube 11 is occluded, $P_2$ will be significantly higher than $P_0$, as shown in FIG. 2, and the alarm 21 will sound. If the tube is not occluded, $P_2$ will be approximately the same as $P_0$, as shown in FIG. 3. There is a threshold in the computer 22 for the difference between $P_0$ and $P_2$, and if the difference is higher than the threshold, then the computer 22 will execute an algorithm for an occlusion.

The tube 11 has a volume, preferably about 0.00724 liters; specifically selected to maximize any monitored pressure difference between the duct 16 and the tube 11. The plurality of selectable flow orifices 14 includes one or more metering orifices 14 to provide specific gas flows, e.g., 0.5 lpm, 1.0 lpm, 2.0 lpm, 4.0 lpm and 8.0 lpm, to the argon handset 23. In the preferred embodiment, the occlusion test is disabled for flow rates above 4.0 lpm. The computer 22 makes the back pressure equalization with the predetermined metered argon gas output a function of the selectable flow rate. That is to say that the back pressure $P_1$ varies as function of the specific flow rate selected.

A method for use of the apparatus 10 within the argon electrosurgery delivery system for detecting an occlusion in a monitored pressure tube 11 connected to a percutaneous passageway into the abdominal cavity 12 of a patient has steps. Supplying argon gas to the output is a step. Connecting the plurality of selectable flow orifices 14 to receive the argon gas supply output is a step. Delivering with one or more of the plurality of selectable flow orifices 14 the predetermined metered argon gas output is a step. Containing within the duct 16 the volume of argon gas by selectively connecting the duct 16 in fluid communication with the predetermined metered argon gas output is a step. Selectively connecting the duct 16 in fluid communication with the percutaneous passageway into the abdominal cavity 12 is a step. Connecting the tube 11 in fluid communication between the percutaneous passageway into the abdominal cavity 12 by connecting the tube 11 to the duct 16 is a step. Connecting the pressure transducer 17 in fluid communication with the duct 16 and periodically connected to the tube 11 and the pressure transducer 17 for periodically receiving and responding with pressure signals from tube 11 is a step. Coupling electrically a control circuit 18 to one or more of the plurality of selectable flow orifices 14 is a step. Equalizing within the tube 11 with the back pressure in response to the pressure signals from the pressure transducer 17 is a step. Connecting the pressure transducer 17 for receiving the tube 11 pressure signals to test equalization is a step. Coupling electrically the electrically operable three way normally closed valve 19 to the control circuit 18 for connecting the pressure transducer 17 and duct 16 to the predetermined metered argon gas output to the abdominal cavity 12 is a step. Coupling electrically the electrically operable three way normally closed valve 19 to the control circuit 18 for alternatively connecting the pressure transducer 17 and duct 16 to the tube 11 to selectively permit periodic fluid communication with the tube 11 to equalize the tube 11 with the predetermined metered argon gas output to the back pressure is a step. Coupling electrically the monitor 20 to the pressure transducer 17 to receive signals from the pressure transducer 17 is a step. Determining periodically with the monitor 20 the rate of pressure change in the tube 11 after the electrically operable three way normally closed valve 19 connects the tube 11 to the pressure transducer 17 and duct 16 is a step. Indicating with the monitor 20 if the pressure in the tube 11 is equalized during a timed interval is a step.

Establishing with the timer 20' in the monitor 20 time intervals for the periodic checking changes in the back pressure in the tube 11 to test equalization is a step. Coupling the alarm 21 to the monitor 20 to indicate lack of pressure equalization between the abdominal cavity 12 and the duct 16 after a test interval of the timer 20' is a step. Connecting the argon electrosurgical handset 23 for laparoscopic application within the abdominal cavity 12 to the predetermined metered argon gas output to the electrically operated three way normally closed valve 19 is a step. The method further includes storing the pressure in the tube 11, $P_0$ in FIGS. 2 and 3, in the computer 22. Thereafter, the method includes the steps of pressurizing the duct 16 with the metered argon gas output 15, and thereafter reconnecting the duct 16 with the tube 11. After the duct 16 and the tube 11 reach equilibrium, $P_2$ in FIGS. 2 and 3, the pressure transducer 17 measures the equilibrium pressure. Further steps in the method include using the computer 22 to compare the stored abdominal cavity 12 pressure, $P_0$, with the equilibrium pressure, $P_2$.

Including one or more metering orifices 14 in the plurality of selectable flow orifices 14 to provide specific gas flows to the argon handset 23 and the electrically operable three way normally closed valve 19 is a step. Making the predetermined metered argon gas output back pressure a function of the selectable flow with the computer 22 is a step. Coupling an audible alarm 21 to the monitor 20 is a step.

While a particular preferred embodiment has been illustrated and described, the scope of protection sought is in the claims that follow.

What is claimed is:

1. An apparatus within an argon electrosurgery delivery system, the apparatus for detecting an occlusion in a monitored pressure tube connected to a percutaneous passageway into the abdominal cavity of a patient, the apparatus comprising:

an argon gas supply output;

a plurality of selectable flow orifices connected to receive the argon gas supply output, one or more of the plurality of selectable flow orifices for delivery of a predetermined metered argon gas output;

a duct for containing a volume of argon gas, the duct selectively connected in fluid communication with the predetermined metered argon gas output, the duct selectively connectable in fluid communication with the percutaneous passageway into the abdominal cavity;

a tube adapted to be connected in fluid communication between the percutaneous passageway into the abdominal cavity and connected to the duct;

a pressure transducer connected in fluid communication with the duct and the duct periodically connected to the tube, the pressure transducer connected for periodically receiving and responding with pressure signals from the tube;

a control circuit coupled electrically to one or more of the plurality of selectable flow orifices for receipt of the predetermined metered argon gas output, the control circuit connected for equalizing within the tube with a back pressure in response to the pressure signals from the pressure transducer, the control circuit electrically coupled to the pressure transducer for receiving the tube pressure signals to test equalization;

an electrically operable a three way normally closed valve electrically coupled to the control circuit for connecting the pressure transducer and duct to the predetermined metered argon gas output to the abdominal cavity, the electrically operable three way normally closed valve coupled to the control circuit for alternatively connecting the pressure transducer and duct to the tube to selectively permit periodic fluid communication with the tube to equalize the tube with the predetermined metered argon gas output to the back pressure; and a monitor electrically coupled to the pressure transducer to receive signals from the pressure transducer, the monitor for periodically determining the rate of pressure change in the tube after the electrically operable three way normally closed valve connects the tube to the pressure transducer and duct, the monitor for indicating if the pressure in the tube is equalized after a timed interval.

2. The apparatus of claim 1 wherein the monitor includes a timer for establishing time intervals for the periodic checking changes in the back pressure in the tube to test equalization.

3. The apparatus of claim 2 wherein an alarm is coupled to the monitor to indicate lack of pressure equalization between the abdominal cavity and the duct after a time interval of the timer.

4. The apparatus of claim 3 wherein the monitor includes a computer to remember the abdominal cavity pressure before connecting the duct and the pressure transducer to the predetermined metered argon gas output, the computer to compare the remembered abdominal cavity pressure with the back pressure after the time interval and following the equalization of the tube to the back pressure.

5. The apparatus of claim 2 wherein the tube has a volume selected to maximize any monitored pressure difference between the duct and the tube.

6. The apparatus of claim 1 wherein the predetermined metered argon gas output connected to the electrically operated three way normally closed valve also connects to an argon electrosurgical handset for laparoscopic application within the abdominal cavity.

7. The apparatus of claim 6 wherein the plurality of selectable flow orifices includes one or more metering orifices to provide specific gas flows to the argon handset and the electrically operable three way normally closed valve.

8. The apparatus of claim 7 wherein the computer makes the back pressure equalization with the predetermined metered argon gas output a function of the selectable flow rate.

9. The apparatus of claim 1 wherein an audible alarm is coupled to the monitor.

10. A method for use of an apparatus within an argon electrosurgery delivery system, the method for detecting an occlusion in a monitored pressure tube connected to a percutaneous passageway into the abdominal cavity of a patient, the method comprising the steps of:

supplying argon gas to an output;

connecting a plurality of selectable flow orifices to receive the argon gas supply output;

delivering with one or more of the plurality of selectable flow orifices a predetermined metered argon gas output;

containing within a duct a volume of argon gas by selectively connecting the duct in fluid communication with the predetermined metered argon gas output;

selectively connecting the duct in fluid communication with the percutaneous passageway into the abdominal cavity;

connecting a tube in fluid communication between the percutaneous passageway into the abdominal cavity by connecting the tube to the duct;

connecting a pressure transducer in fluid communication with the duct and periodically connected to the tube and the pressure transducer for periodically receiving and responding with pressure signals from tube;

coupling electrically a control circuit to one or more of the plurality of selectable flow orifices;

equalizing within the tube with a back pressure in response to the pressure signals from the pressure transducer;

connecting the pressure transducer for receiving the tube pressure signals to test equalization;

coupling electrically an electrically operable three way normally closed valve to the control circuit for connecting the pressure transducer and duct to the predetermined metered argon gas output to the abdominal cavity;

coupling electrically the electrically operable three way normally closed valve to the control circuit for alternatively connecting the pressure transducer and duct to the tube to selectively permit periodic fluid communication with the tube to equalize the tube with the predetermined metered argon gas output to the back pressure;

coupling electrically a monitor to the pressure transducer to receive signals from the pressure transducer;

determining periodically with the monitor the rate of pressure change in the tube after the electrically operable three way normally closed valve connects the tube to the pressure transducer and duct; and indicating with the monitor if the pressure in the tube is equalized during a timed interval.

11. The method of claim 10 with the step of establishing with a timer in the monitor time intervals for the periodic checking changes in the back pressure in the tube to test equalization.

12. The method of claim 11 with the step of coupling an alarm to the monitor to indicate lack of pressure equalization between the abdominal cavity and the duct after a time interval of the timer.

13. The method of claim 12 with the step of including a computer in the monitor to remember the abdominal cavity pressure before connecting the predetermined metered argon gas output and the pressure transducer to the predetermined metered argon gas output, the computer to compare the remembered abdominal cavity pressure with the back pressure following the equalization of the tube to the back pressure.

14. The method of claim 11 with the step of maximizing with a selected volume for the tube any monitored pressure difference between the duct and the tube.

15. The method of claim 10 with the step of connecting an argon electrosurgical handset for laparoscopic application within the abdominal cavity to the predetermined metered argon gas output to the electrically operated three way normally closed valve.

16. The method of claim 15 with the step of including one or more metering orifices in the plurality of selectable flow orifices to provide specific gas flows to the argon handset and the electrically operable three way normally closed valve.

17. The method of claim 16 with the step of making the predetermined metered argon gas output back pressure a function of the selectable flow with the computer.

18. The method of claim 10 with the step of coupling an audible alarm to the monitor.

* * * * *